US00PP30348P2

(12) United States Plant Patent
Hansen

(10) Patent No.: US PP30,348 P2
(45) Date of Patent: Apr. 2, 2019

(54) ***SEDUM* PLANT NAMED 'PLUM DAZZLED'**

(50) Latin Name: ***Sedum* hybrid**
Varietal Denomination: Plum Dazzled

(71) Applicant: Christopher M. Hansen, Zeeland, MI (US)

(72) Inventor: Christopher M. Hansen, Zeeland, MI (US)

( * ) Notice: Subject to any disclaimer, the term of this patent is extended or adjusted under 35 U.S.C. 154(b) by 0 days.

(21) Appl. No.: 15/732,222

(22) Filed: Oct. 5, 2017

(51) Int. Cl.
*A01H 5/02* (2018.01)

(52) U.S. Cl.
USPC ..... Plt./479

(58) Field of Classification Search
USPC ..... Plt./479
See application file for complete search history.

*Primary Examiner* — Keith O. Robinson
(74) *Attorney, Agent, or Firm* — Penny J. Aguirre

(57) ABSTRACT

A new cultivar of *Sedum* plant named 'Plum Dazzled' that is characterized by its very compact plant habit with stems that do not flop, it reaches about 23 cm (9 inches) in height and 46 cm (18 inches) in spread, its foliage that emerges medium gray-blue in spring and turns to very dark purple-black in mid summer, its flowers that are raspberry pink in color, and its high resistance to *Sedum* foliage blight and powdery mildew.

2 Drawing Sheets

Botanical classification: *Sedum* hybrid.
Variety denomination: 'Plum Dazzled'.

BACKGROUND OF THE INVENTION

The present invention relates to a new and distinct cultivar of *Sedum* plant, botanically of hybrid origin and known as *Sedum* 'Plum Dazzled' referred to hereinafter by its cultivar name, 'Plum Dazzled'. The new cultivar of *Sedum* is a hardy herbaceous perennial grown for use as a landscape and container plant and is particularly suitable as a groundcover.

'Plum Dazzled' arose from an ongoing breeding program conducted by the Inventor in Hudsonville, Mich. The goal of the breeding program is to produce new groundcover type cultivars of *Sedum* with compact, mounding, plant habits without the tendency to flop combined with dark purple foliage and abundant, large, and brightly colored raspberry pink flower heads.

The inventor made a cross in September 2008 between an unnamed, unpatented plant from the Inventor's breeding program as the female parent and 'Zenox' (U.S. Plant Pat. No. 16,888) as the male parent. 'Plum Dazzled' was selected as a single unique plant in September 2012 amongst the seedlings that resulted from the above cross.

Asexual propagation of the new cultivar was first accomplished by stem tip cuttings in May of 2009 in Hudsonville, Mich. Propagation by tip stem cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'Plum Dazzled' as a unique cultivar of *Sedum*.

1. 'Plum Dazzled' exhibits a very compact plant habit with stems that do not flop.

2. 'Plum Dazzled' reaches about 23 cm (9 inches) in height and 46 cm (18 inches) in spread.
3. 'Plum Dazzled' exhibits foliage that emerges medium gray-blue in spring and turns to very dark purple-black in mid summer.
4. 'Plum Dazzled' exhibits flowers that are raspberry pink in color.
5. 'Plum Dazzled' has been observed to be highly resistant to *Sedum* foliage blight and powdery mildew.

The female parent of 'Plum Dazzled' differs from 'Plum Dazzled' in having a smaller plant size (reaches 10 cm in height), inflorescences that are much smaller in size, smaller leaves, and gray-green foliage that does not change to dark purple-black in summer. The male parent, 'Zenox', differs from 'Plum Dazzled' in being larger in size (70% larger) and less compact, in having flowers that are light pink in color, and in having larger leaves (70% larger). 'Plum Dazzled' can also be most closely compared to the cultivars 'Sunset Cloud' (not patented) and 'Dazzleberry' (U.S. Plant Pat. No. 22,457). 'Sunset Cloud' and 'Dazzleberry' are similar to 'Plum Dazzled' in being a groundcover-type *Sedum* and in having medium dark gray foliage that turns purple in color. 'Sunset Cloud' differs from 'Plum Dazzled' in having purple foliage that is about 35% lighter in color with leaves that are smaller, less thick and dense, a taller plant height (30 cm) and a floppy plant habit. 'Dazzleberry' differs from 'Plum Dazzled' in having purple foliage that is about 35% lighter in color, an earlier blooming season (blooming 2 to 3 weeks earlier) and leaves that are slightly larger in size.

BRIEF DESCRIPTION OF THE DRAWINGS

The accompanying colored photographs illustrate the overall appearance and distinct characteristics of the new *Sedum*. The photographs were taken of plants about 9 months in age as grown outdoors in 1-gallon containers in Hudsonville, Mich.

The photograph in FIG. 1 provides a side view comparison of 'Dazzleberry' (left) and 'Plum Dazzled' (right) and depicted the more intense dark purple-black foliage of 'Plum Dazzled'.

Figure 1:
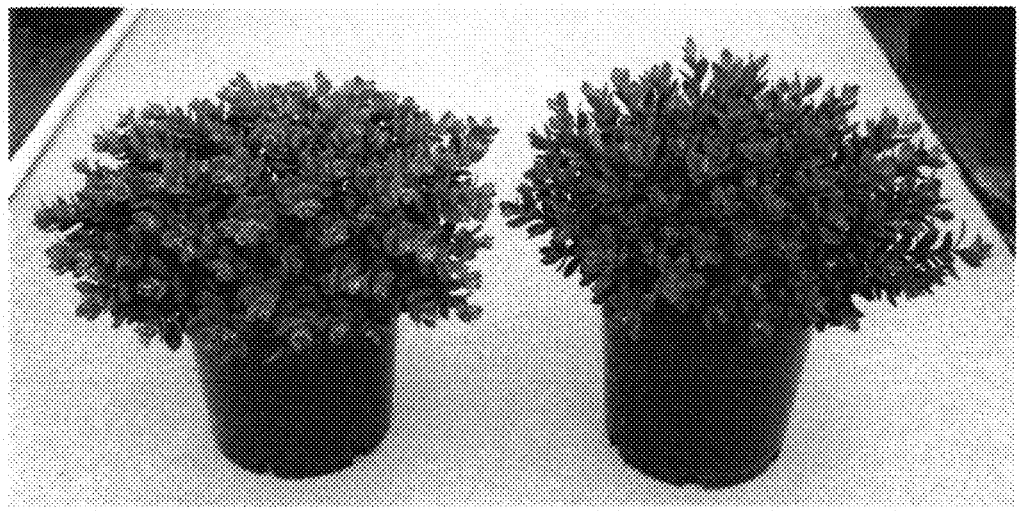
Figure 2:
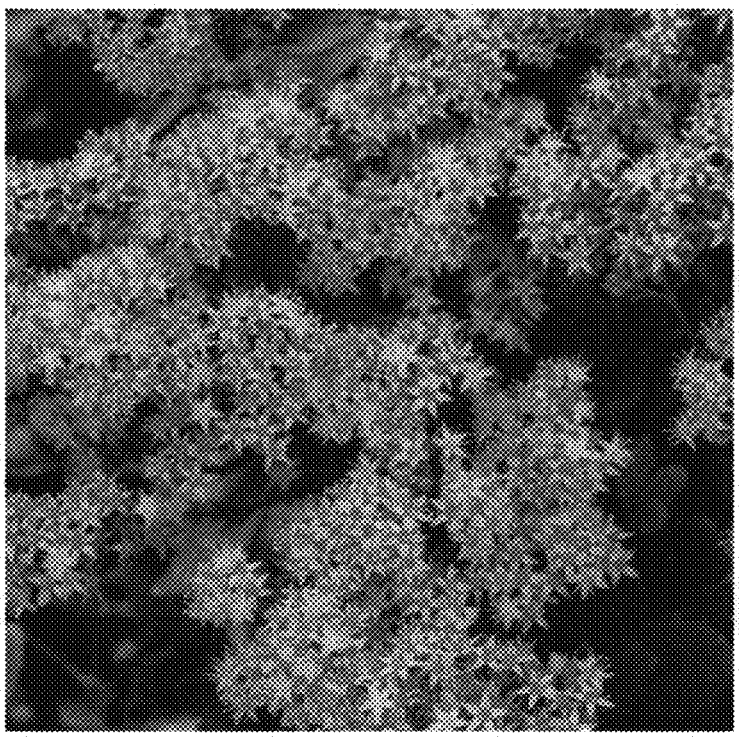

The photograph in FIG. 2 provides a close up view of the inflorescences of 'Plum Dazzled'.

Figure 3:
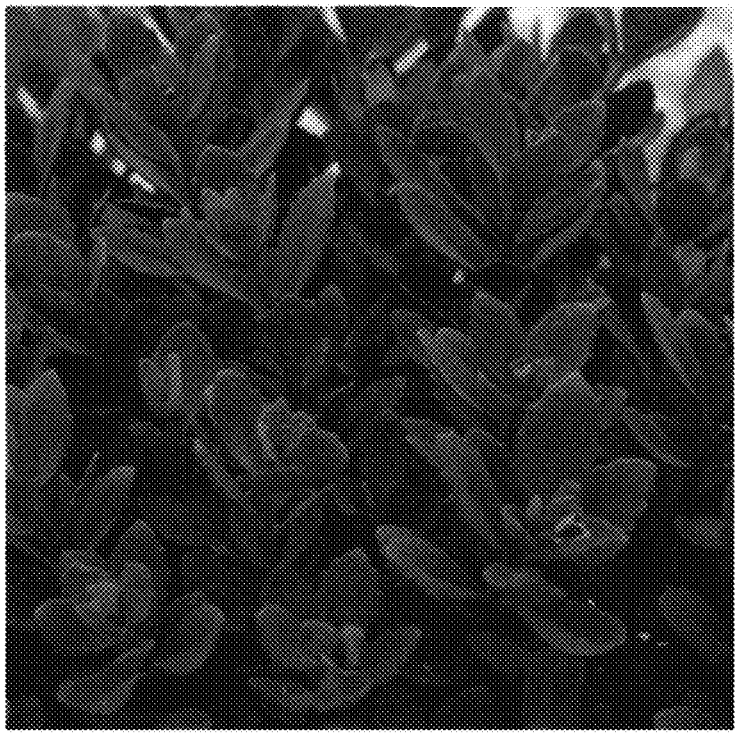

The photograph in FIG. 3 provides a close up view of the foliage of 'Plum Dazzled'.

The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 6 month-old plants of 'Plum Dazzled' as grown outdoors in 2-qt containers in Hudsonville, Mich. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—5 weeks in mid summer in Michigan.

*Plant type.*—Herbaceous perennial.

*Plant habit.*—Widely spreading, mounded.

*Height and spread.*—Reaches an average of 23 cm in height and 46 cm in spread as a mature plant in the landscape.

*Hardiness.*—At least hardy in U.S.D.A. Zones 4 to 9.

*Diseases pest.*—Highly resistant to *Sedum* foliage blight (caused by *Septoria sedi*) and powdery mildew (caused by *Erysiphe cichoracearum*), no occurrence of either has been observed during the 9 years of observation.

*Root description.*—Fibrous, 159C in color.

*Propagation.*—Tip stem cuttings.

*Root development.*—Roots initiate in 15 days and a young plant is fully rooted in a 4-inch container in about 60 days.

*Growth rate.*—Vigorous.

Stem description:

*Stem shape.*—Oval.

*Stem size.*—An average of 10 cm in length (excluding inflorescence), 4 mm in width.

*Internode length.*—Average of 1.5 cm.

*Stem color.*—Young branches; a blend of 195A and 182B, mature branches; 183A.

*Stem surface.*—Glabrous and slightly shiny.

*Branching habit.*—An average of 12 branches per plant.

Foliage description:

*Leaf shape.*—Obtuse.

*Leaf division.*—Simple.

*Leaf arrangement.*—Opposite.

*Leaf base.*—Acute.

*Leaf apex.*—Acute to rounded.

*Leaf venation.*—Not conspicuous.

*Leaf margins.*—Entire and moderately serrulate.

*Leaf attachment.*—Most leaves are Petiolate, some are sessile.

*Leaf number.*—An average of 18 leaves per branch.

*Leaf orientation.*—Nearly horizontal to slightly upward, slightly cupped.

*Leaf texture.*—Thick, succulent.

*Leaf surface.*—Both surfaces dull and glaucous.

*Leaf color.*—Spring and summer upper and lower surface; 189B, late summer and fall upper and lower surface; a blend of N189B to N189A, 200A, and N187A.

*Leaf size.*—Average of 3.5 cm in length and 1.5 cm in width.

*Petiole.*—An average of 3 mm in length and 3 mm in diameter, surface texture glabrous and slightly shiny, 183A in color.

Flower description:

*Inflorescence type.*—Dense, slightly rounded cymes with an average of 3 terminal forked branches at terminus and upper lateral nodes, blooms are present on top of the plant.

*Inflorescence size.*—An average of 4 cm in diameter and 5 cm in depth (inclusive of forked branches) per individual cymes and up to 9 cm in length and 6 cm in width for the compound cyme, and up to 17 cm in width and 10 cm in depth for all cymes on a stem.

*Lastingness of inflorescence.*—At least one month.

*Flower type.*—Perfect, spreading, 5-starred.

*Flower number.*—An average of 40 flowers per branched cyme, an average of 10 to 20 flowers per stem.

*Flower fragrance.*—None.

*Flower buds.*—Ovate in shape, about 5 mm length and 2 mm in width, glabrous surface, 185A and striped 194A in color.

*Flower size.*—About 4 mm in depth and 1 cm in diameter.

*Peduncles.*—Round in shape, an average of 1.5 cm in length and 1 mm in width, secondary average 2 mm in length and 0.5 mm in width, 187A in color, glabrous surface, very strong.

*Pedicels.*—Round in shape, an average of 5 mm in length and 0.5 mm in width, 187A in color, glabrous surface, strong.

*Calyx.*—5-parted.

*Sepals.*—5, tube; about 1 mm in length and width, color; N189B, flushed with 187A, lanceolate in shape, entire margin, narrowly acute apex, fused base, glaucous on both surfaces.

*Petals.*—5, spreading, 3 mm in length and 1 mm in width, lanceolate in shape, rounded base, acute apex, entire margin, color; inner surface when opening and fully open; base 76D, rest of surface a blend of 71A and N74A, outer surface when opening and fully open; base 76D, rest of surface a blend of N74A and 71A, glabrous on both surfaces.

Reproductive organs:

*Pistils.*—5, showy, held erect, about 3 mm in length 1 mm in width, stigma; minute, smaller than 0.5 mm and 161A in color, style; ovate, rounded in shape, cone like, and N74A in color, ovary; small, single celled and translucent in color.

*Stamens.*—10, about 4 mm in length, filament; very fine, N74A in color, anther; club shaped, about 0.5 mm in length and width, 161A in color, pollen is moderate in quantity and N74A in color.

*Fruit.*—Fruit and seed production has not been observed to date.

It is claimed:

1. A new and distinct variety of *Sedum* plant named 'Plum Dazzled' as described and illustrated herein.

* * * * *